(12) United States Patent
Govea

(10) Patent No.: US 9,005,503 B2
(45) Date of Patent: Apr. 14, 2015

(54) METHODS OF MANUFACTURING A CONTACT ARRAY ASSEMBLY AND LEADS AND SYSTEMS CONTAINING THE ASSEMBLY

(71) Applicant: Boston Scientific Neuromodulation Corporation, Valencia, CA (US)

(72) Inventor: Michael Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/100,509

(22) Filed: Dec. 9, 2013

(65) Prior Publication Data

US 2014/0167317 A1 Jun. 19, 2014

Related U.S. Application Data

(60) Provisional application No. 61/737,011, filed on Dec. 13, 2012.

(51) Int. Cl.
*A61N 1/05* (2006.01)
*B29C 45/14* (2006.01)

(52) U.S. Cl.
CPC ............ *A61N 1/05* (2013.01); *B29C 45/14467* (2013.01); *B29C 45/14639* (2013.01); *A61N 1/0534* (2013.01); *A61N 1/0551* (2013.01)

(58) Field of Classification Search
None
See application file for complete search history.

(56) References Cited

U.S. PATENT DOCUMENTS

| 6,181,969 | B1 | 1/2001 | Gord |
|---|---|---|---|
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,437,193 | B2 | 10/2008 | Parramon et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,364,278 | B2 | 1/2013 | Pianca et al. |
| 2007/0150036 | A1 | 6/2007 | Anderson |
| 2009/0248124 | A1* | 10/2009 | Pianca et al. ................ 607/116 |
| 2010/0057175 | A1* | 3/2010 | McDonald et al. ........... 607/116 |
| 2010/0070009 | A1* | 3/2010 | Barker .......................... 607/117 |
| 2010/0256694 | A1* | 10/2010 | Barker .............................. 607/2 |
| 2010/0304626 | A1* | 12/2010 | McDonald ................... 439/877 |
| 2010/0331934 | A1* | 12/2010 | McDonald et al. ........... 607/116 |
| 2011/0293971 | A1* | 12/2011 | Ho et al. .......................... 429/7 |

* cited by examiner

*Primary Examiner* — Jacob Thomas Minskey
(74) *Attorney, Agent, or Firm* — Lowe Graham Jones PLLC; Bruce E. Black

(57) ABSTRACT

A method of making an electrical stimulation lead includes disposing conductive contacts in a spaced-apart longitudinal arrangement within a mold. A portion of a stylet tube is disposed within the mold, and the stylet tube extends through the conductive contacts. Conductive wires are positioned external to the stylet tube and each contact is coupled to at least one of the wires. A non-conductive material is molded between adjacent pairs of the contacts, around the wires, and over the stylet tube, to form a portion of the lead. This portion includes the contacts, the stylet tube, the wires, and one or more non-conductive spacers formed from the non-conductive material. Finally, the portion of the lead is removed from the mold. Another method includes placing a temporary tube around the conductive contacts and forming spacers by introducing flowable, curable, non-conductive material within the tube and between the conductive contacts.

10 Claims, 8 Drawing Sheets

METHODS OF MANUFACTURING A CONTACT ARRAY ASSEMBLY AND LEADS AND SYSTEMS CONTAINING THE ASSEMBLY

CROSS-REFERENCE TO RELATED APPLICATIONS

This application claims the benefit under 35 U.S.C. §119 (e) of U.S. Provisional Patent Application Ser. No. 61/737,011 filed Dec. 13, 2012, which is incorporated herein by reference.

FIELD

The present invention is directed to the area of implantable electrical stimulation systems and methods of making and using the systems. The present invention is also directed to methods of making a contract array assembly for an implantable stimulation lead, as well as methods of making and using the leads and electrical stimulation systems containing the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method of making an electrical stimulation lead that includes disposing conductive contacts in a spaced-apart longitudinal arrangement within a mold. A portion of a stylet tube is also disposed within the mold, and the stylet tube extends longitudinally through the conductive contacts. Conductive wires are positioned external to the stylet tube and each conductive contact is coupled to at least one of the conductive wires. A non-conductive material is then molded between adjacent pairs of the conductive contacts, around the conductive wires, and over the stylet tube, to form a portion of the electrical stimulation lead. This portion includes the conductive contacts, the stylet tube, the conductive wires, and one or more non-conductive spacer formed from the non-conductive material. Finally, the portion of the electrical stimulation lead is removed from the mold.

Another embodiment is a method of making an electrical stimulation lead that includes disposing conductive contacts in a spaced-apart longitudinal arrangement on a conductor guide or a stylet guide. Conductive wires are disposed within the conductor guide or around the stylet guide, and each conductive contact is coupled to at least one of the conductive wires. A temporary tube is disposed over the conductive contacts and a flowable non-conductive material is introduced into the temporary tube. The non-conductive material flows between adjacent pairs of conductive contacts and over the conductor guide or stylet tube. One or more spacers are formed from the flowable non-conductive material to separate the conductive contacts. The temporary tube is removed to expose the conductive contacts.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to methods of making a contract array assembly for an implantable stimulation lead, as well as methods of making and using the leads and electrical stimulation systems containing the leads.

Suitable implantable electrical stimulation systems include, but are not limited to, a least one lead with one or more electrodes disposed along a distal end of the lead and one or more terminals disposed along the one or more proximal ends of the lead.

Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
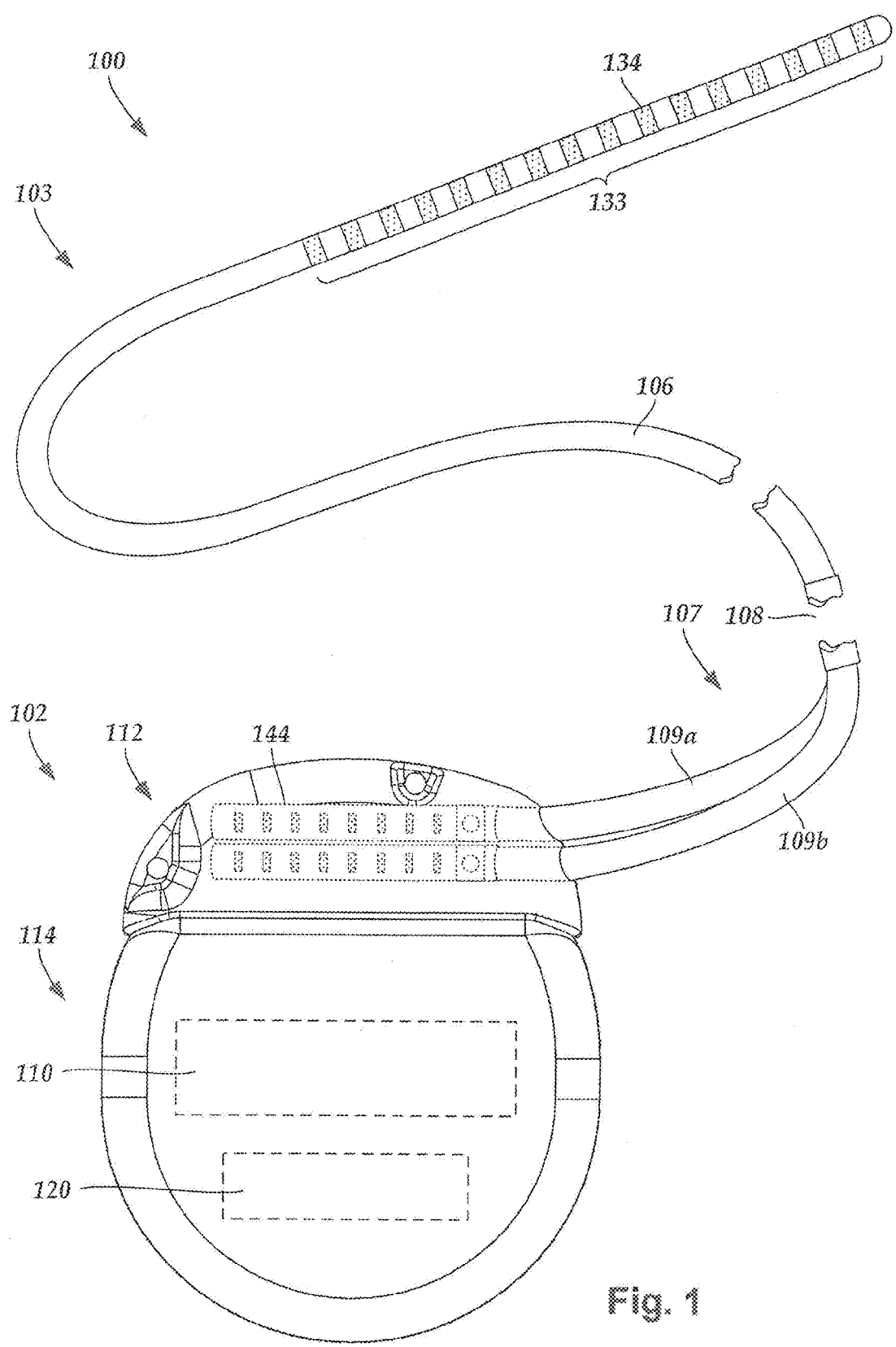
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system 100 or components of the electrical stimulation system 100, including one or more of the lead bodies 106 and the control module 102, are typically implanted into the body of a patient. The electrical stimulation system 100 can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. However, other numbers of electrodes 134 may also be used.

The electrodes 134 of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
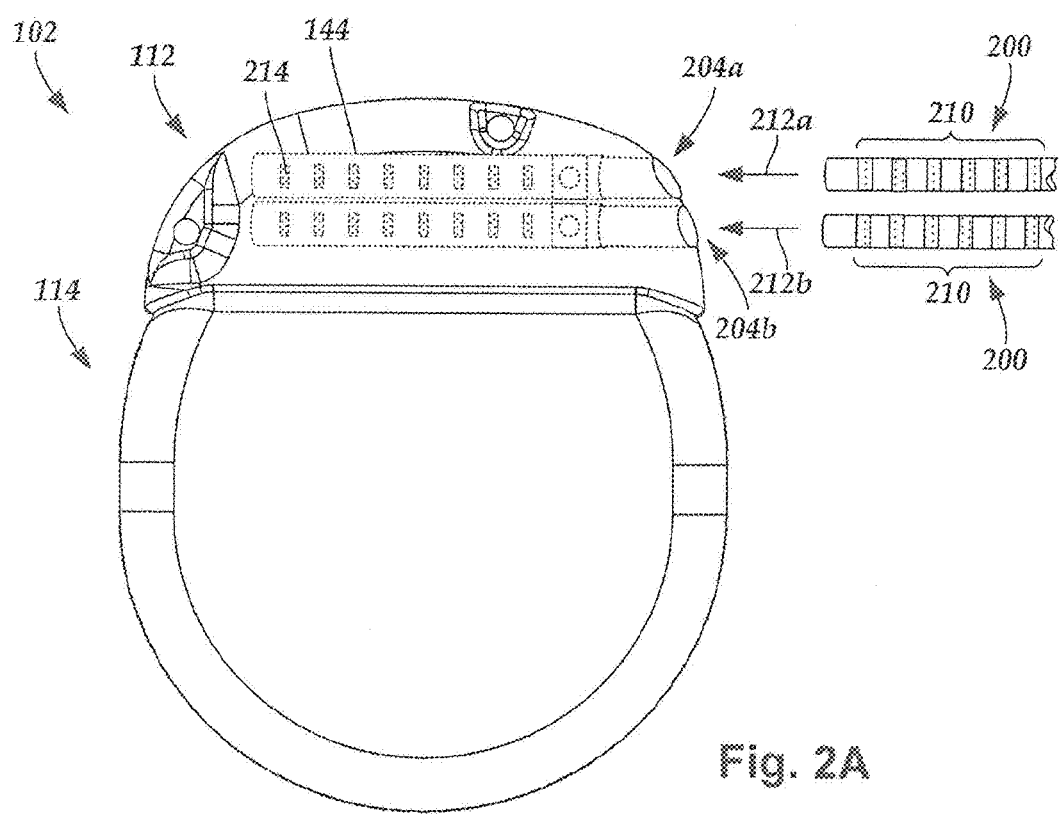
FIG. 2A is a schematic side view of one embodiment of the control module of FIG. 1 configured and arranged to electrically couple to an elongated device, according to the invention.
Figure 2B:
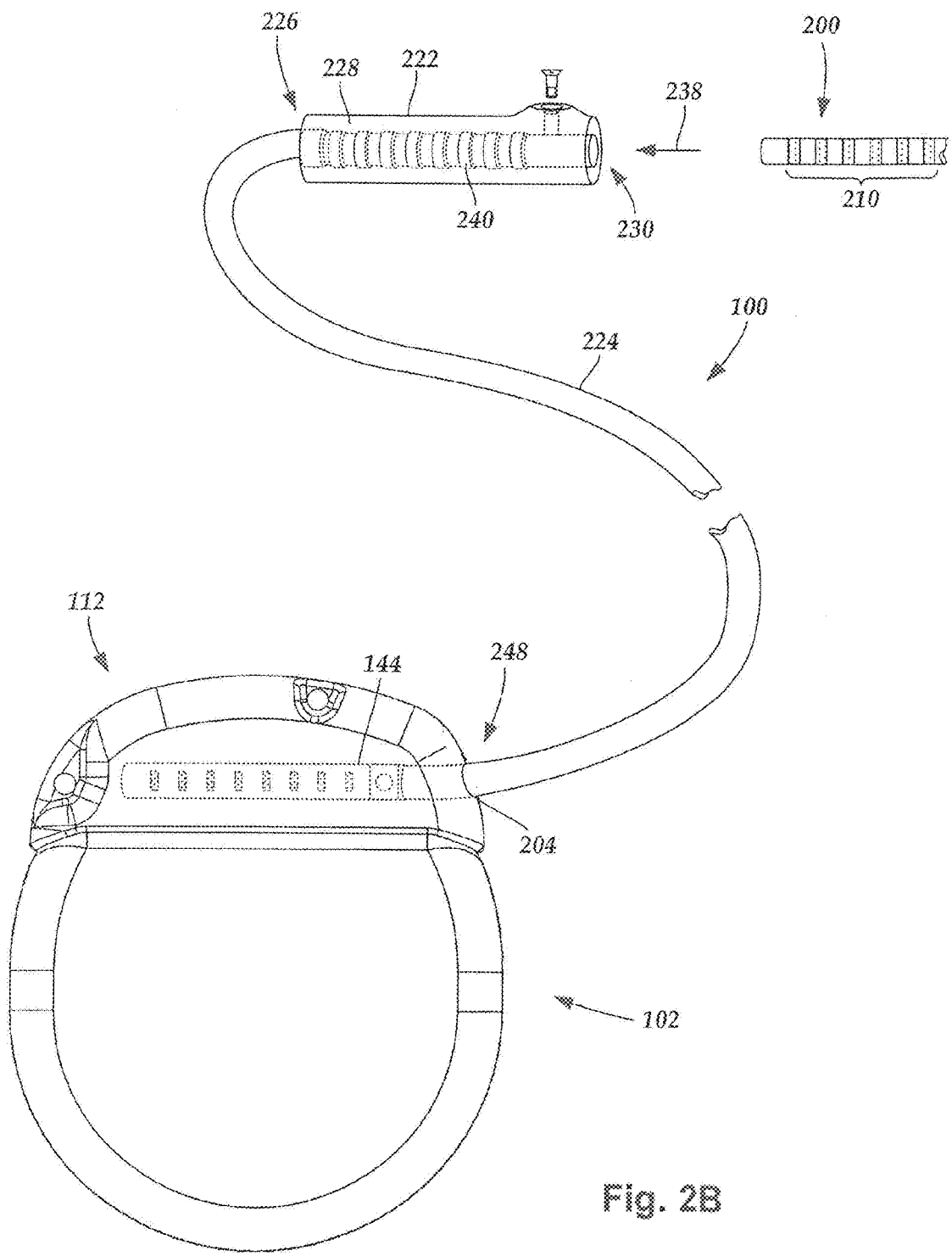
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts 214 or 240 are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the lead body 106, for example, for inserting a stylet to facilitate placement of the lead body 106 within a body of a patient. Additionally, there may also be one or more lumens (not shown) that open at, or near, the distal end of the lead body 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices 200 may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contacts 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

Further, a lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3A:
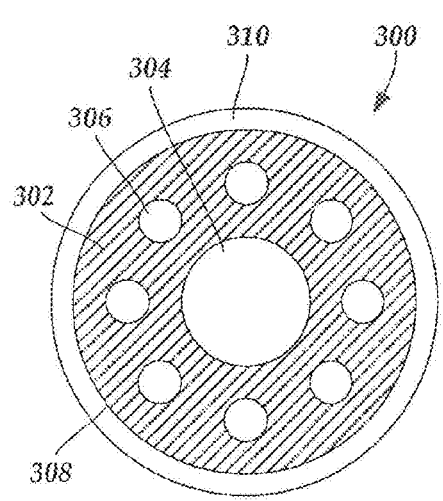
FIG. 3A is a schematic transverse cross-sectional view of one embodiment of the lead of FIG. 1, the lead including a multi-lumen conductor guide that defines a central lumen and a plurality of conductor lumens arranged around the central lumen, according to the invention.

Turning to FIG. 3A, in at least some embodiments, the lead includes a lead body with an elongated multi-lumen conductor guide having one or more conductor lumens (preferably, multiple conductor lumens) arranged about a central lumen. In at least some embodiments, the conductor lumens are arranged about the central lumen such that there are no other lumens extending along the multi-lumen conductor guide between the central lumen and each of the multiple conductor lumens. In some embodiments, the conductor lumens are each configured and arranged to receive a single conductor. In other embodiments, at least one of the conductor lumens is configured and arranged to receive multiple conductors.

FIG. 3A is a transverse cross-sectional view of one embodiment of the lead 300 including an elongated multi-lumen conductor guide 302. The multi-lumen conductor guide 302 may extend an entire longitudinal length of the lead 300 from the electrodes 134 (FIG. 1) to the terminals 210 (FIG. 2A). As shown in FIG. 3A, the multi-lumen conductor guide 302 defines a central lumen 304 and a plurality of conductor lumens, such as conductor lumen 306. The conductor lumens can have any suitable cross-sectional shape (e.g., round, oval, rectangular, triangular, or the like).

In at least some embodiments, the plurality of conductor lumens 306 are encapsulated by the multi-lumen conductor guide 302 such that the conductor lumens 306 do not extend to an outer surface 308 of the multi-lumen conductor guide 302. Further, when conductors (320 in FIG. 3B) are disposed in the conductor lumens 306, the conductors are not exposed along the outer surface 308 of the multi-lumen conductor guide 302. The central lumen 304 and the plurality of conductor lumens 306, however, can be arranged in any suitable manner. In preferred embodiments, the conductor lumens 306 are disposed in the multi-lumen conductor guide 302 such that the conductor lumens 306 are peripheral to the central lumen 304. In at least some embodiments, the lead 300 may include one or more outer coatings of material 310 disposed over the outer surface 308 of multi-lumen conductor guide 302.

Further, the plurality of conductor lumens 306 are configured and arranged to receive conductors, which electrically couple the electrodes 134 (FIG. 1) to the terminals 210 (FIG. 2A).

Figure 3B:
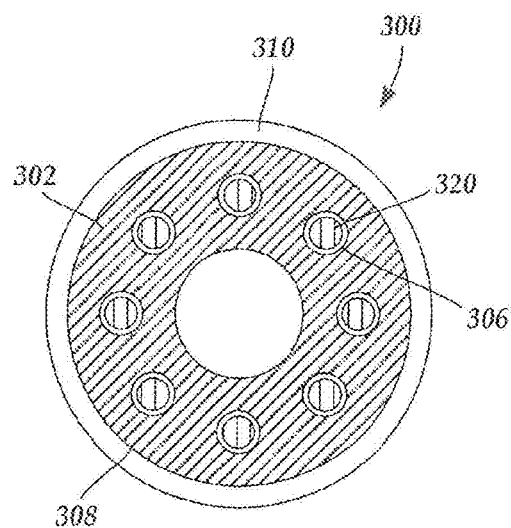
FIG. 3B is a schematic transverse cross-sectional view of one embodiment of conductors disposed in each of a plurality of conductor lumens of the multi-lumen conductor guide of FIG. 3A such that a different single conductor is disposed in each of the conductor lumens, according to the invention.

FIG. 3B is a transverse cross-sectional view of one embodiment of conductors, such as conductor 320, disposed in the conductor lumens 306. A multi-lumen conductor guide 302 can be formed of any suitable material including, but not limited to, polyurethane, silicone, or silicone-polyurethane copolymer. It will be recognized that the multi-lumen conductor guide 302 need not have the specific form illustrated in FIGS. 3A and 3B and that other conductor guide arrangements can be used including arrangements that permit more than one conductor per lumen or includes fewer conductor lumens (in some instances, a single conductor lumen). In some embodiments, the conductor guide 302 may be formed around the conductors 320 by molding or other methods. In some embodiments, the conductor guide 302 may be formed first and then the conductors 320 can be inserted into the conductor guide 302.

Figure 4A:
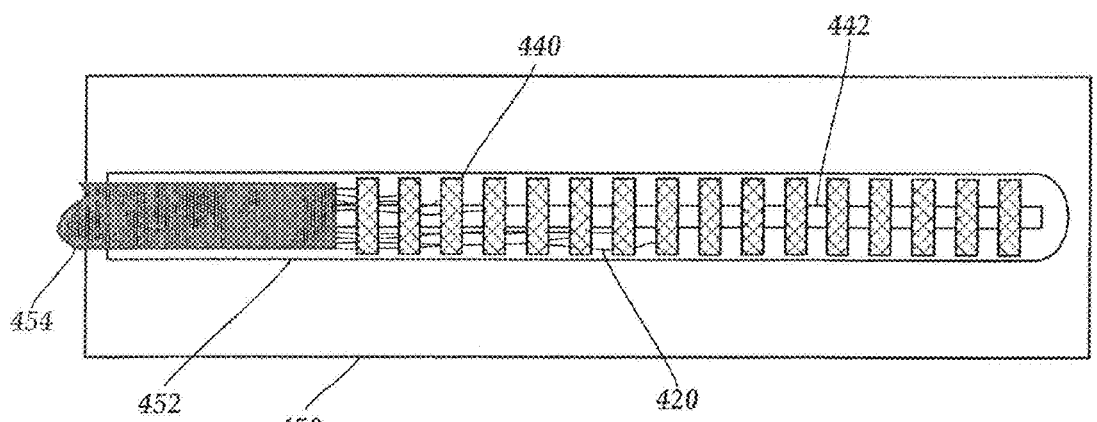
FIG. 4A is a schematic top view of one embodiment of conductive contacts, conductive wires, and a stylet tube disposed in a mold, according to the invention (for clarity of illustration conductive wires coupled to only the left eight conductive contacts are illustrated, it will be understood that additional conductive wires are coupled to the right eight conductive contacts)
Figure 4B:
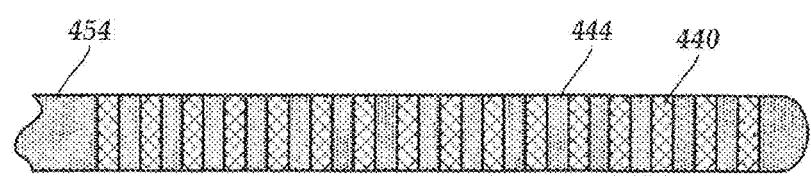
FIG. 4B is a schematic side view of one embodiment of a portion of a lead formed using the components and mold of FIG. 4A, according to the invention.

FIGS. 4A-4B illustrate one method of forming a contact array of a lead. FIG. 4A illustrates conductive contacts 440, conductive wires 420, and a stylet tube 442 disposed in a mold 450. (Only the bottom portion of the mold 450 is illustrated in FIG. 4A, but it will be understood that there is a corresponding top portion that fits over the bottom portion and the components disposed in the mold.) The mold 450 includes a mold cavity 452 which may include individual cavities for each of the conductive contacts 440 and cavities for spacers (which will be formed by molding) disposed between the cavities for the conductive contacts 440. Although explicitly not shown, the mold 450 typically has one or more injection ports for injecting a molding material into the mold 450.

The mold 450 can be made of any suitable material including, but not limited to, metals or alloys, including stainless steel, rigid plastics, and the like. Further, the mold 450 can be formed of any appropriate shape, such as, rectangular, elliptical, cylindrical, and the like, and combinations thereof.

The conductive contacts 440 are positioned in a longitudinally spaced apart configuration within the mold 450. The positioning of the conductive contacts 440 along the length of the lead is such that adjacent conductive contacts 440 may be spaced apart from each other by a specific distance. When disposed at the distal end of an electrical stimulation lead, the conductive contacts 440 are electrodes. When disposed at the proximal end of an electrical stimulation lead, the conductive contacts 440 are terminals. In the illustrated embodiment, the conductive contacts 440 are ring-shaped. However, other suitable shapes of the conductive contacts 440 include, but are not limited to, rectangular, square, elliptical, oval, and the like.

A stylet tube 442 is preferably disposed within the mold 450 and extends longitudinally through the ring-shaped conductive contacts 440. The stylet 442 defines a lumen within the electrical stimulation lead through which a stylet can be inserted, particularly during implantation of the lead. Any suitable material can be used for the stylet tube 442 including, for example, biocompatible polymer materials such as PEEK, polyurethane, silicone, and the like.

Conductive wires 420 couple to the conductive contacts 440. Each of the conductive contacts 440 may be coupled to one or more of the conductive wires 420. The conductive wires 420 extend outwards from the conductor lumens 306 (shown earlier in FIG. 3A) of the lead body 454, and are positioned external to the stylet tube 442. Further, each conductive wire 420 extends along the longitudinal axis of the stylet tube 442. Any suitable method may be used to couple the conducting wires 420 to the conductive contacts 440, such as welding, soldering, or the like. In some embodiments, the conductive wires 420 may be coiled around the stylet tube 442.

A non-conductive material is injected into the mold 450 into the space disposed between each pair of adjacent conductive contacts of the conductive contacts 440, around the conductive wires 420, and over the stylet tube 442, to form a portion of the electrical stimulation lead 103. The non-conductive material forms spacers 444 between the conductive contacts 440, electrically isolating the conductive contacts 440 from each other, as illustrated in FIG. 4B. The non-conductive molding material may possess any flowable form which can be cured or otherwise solidified. Suitable examples of the non-conductive material include silicone, polyurethane, and the like. In at least some embodiments, the non-conductive material may be reflowable after solidification by, for example, heating.

Once the spacers 444 are formed between the conductive contacts 440, around the conductive wires 420, and over the stylet tube 442, the electrical stimulation lead is removed from the mold 450, as illustrated in FIG. 4B.

Figure 5A:
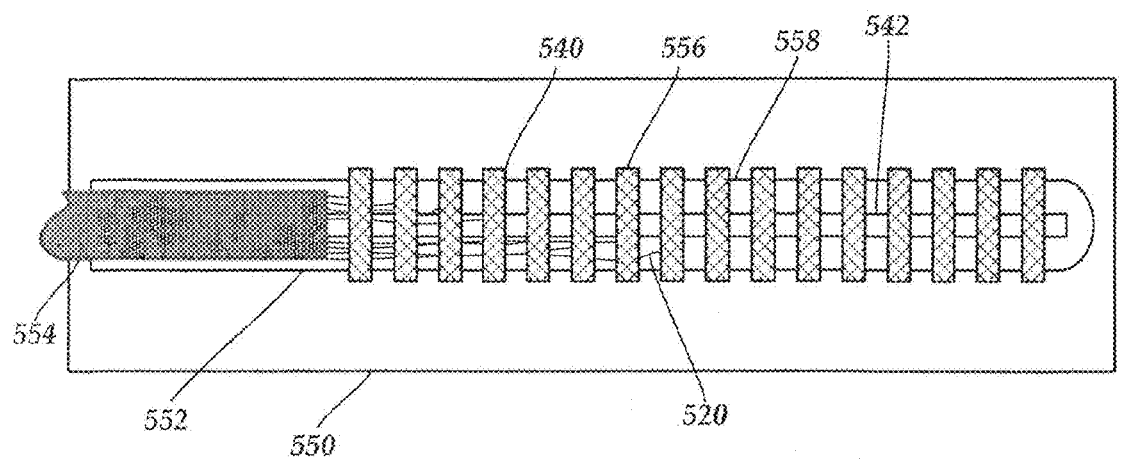
FIG. 5A is a schematic top view of another embodiment of conductive contacts, conductive wires, and a stylet tube disposed in a mold, according to the invention (for clarity of illustration conductive wires coupled to only the left eight conductive contacts are illustrated, it will be understood that additional conductive wires are coupled to the right eight conductive contacts)
Figure 5B:
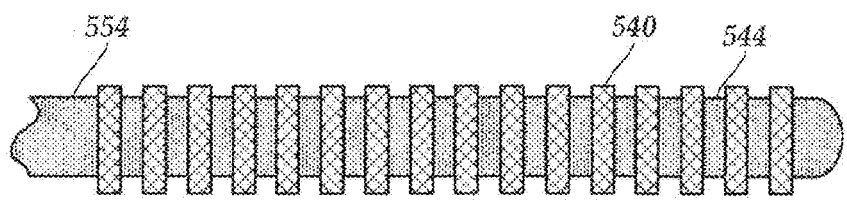
FIG. 5B is a schematic side view of one embodiment of a portion of a lead formed using the components and mold of FIG. 5A prior to grinding, according to the invention.
Figure 5C:
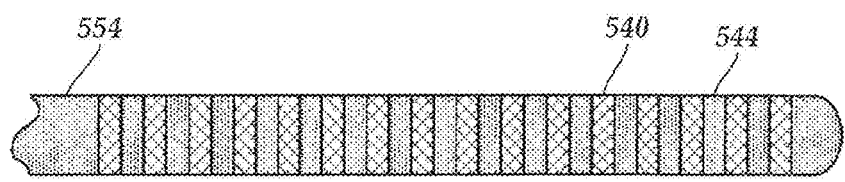
FIG. 5C is a schematic side view of one embodiment of a portion of a lead formed using the components and mold of FIG. 5A after grinding, according to the invention.

FIGS. 5A-5C illustrate another method of forming a contact array of a lead. Conductive contacts 540, conductive wires 520, and a stylet tube 542 are disposed in a mold 550, as illustrated in FIG. 5A. (Only the bottom portion of the mold 550 is illustrated in FIG. 5A, but it will be understood that there is a corresponding top portion that fits over the bottom portion and the components disposed in the mold.) The mold 550 includes a mold cavity 552 having contact cavities 556 that receive the conductive contacts 540 and spacer cavities 558 in which spacers will be formed by molding. Each spacer cavity 558 is positioned between the adjacent pairs of the contact cavities 556. In at least some embodiments, the outer diameter of the spacer cavities 558 is smaller than that of the contact cavities 556, as illustrated in FIG. 5A. In other embodiments, the outer diameter of the spacer cavities may be the same as, or larger than, the outer diameter of the contact cavities 556. Further, the number of cavities within the mold 550 may vary, depending upon the number of conductive contacts (i.e., electrodes/terminals).

When disposed within the contact cavities 556 of the mold 550, the conductive contacts 540 are longitudinally spaced apart from each other. In at least some embodiments, adjacent conductive contacts 540 are separated from each other by a specific distance.

At least a portion of a stylet tube 542 is disposed within the mold 550. The stylet tube 442 extends longitudinally through the conductive contacts 540. The conductive wires 520 extend outwards from the different conductor lumens 306 (shown earlier in FIG. 3A) of the lead body 554 and are disposed external to the stylet tube 542. The conductive wires 520 are coupled to the conductive contacts 540. In some embodiments, the conductive wires 520 may be coiled around the stylet tube 542.

A flowable non-conductive material is injected into the mold 550, through one or more injection ports (not shown) provided in the mold 550. The non-conductive material fills the spaces between adjacent pairs of the conductive contacts 540, around the conductive wires 520, and over the stylet tube 542. Once the non-conductive material cured or otherwise solidified to form the spacers 544, the portion of the electrical stimulation lead is removed from the mold 550, as illustrated in FIG. 5B.

In the embodiment illustrated in FIG. 5B, the conductive contacts 540 have a diameter greater than the outer diameter of the spacers 544. This difference is due to smaller outer diameter of the spacer cavities 558 (FIG. 5A) than that of the contact cavities 556 (FIG. 5A). In other embodiments, the spacers may have the same or larger diameter than the conductive contacts.

A portion of the conductive contacts 540 may be removed so that the conductive contacts 540 and the spacers 544 have the same diameter, as illustrated in FIG. 5C. Any suitable technique can be used to remove the outer portion of the conductive contacts including, but not limited to, grinding (for example, centerless grinding). These techniques may also remove a portion of the spacer to provide a finished surface to the spacers and conductive contacts. It will also be recognized that the same techniques can be used to remove an outer portion of the spacers if the spacers have a larger diameter than the conductive contacts. FIG. 5C depicts the finished outer surface of the lead and lead body 554 where the conductive contacts 540 and the spacers 544 are isodiametric.

Figure 6A:
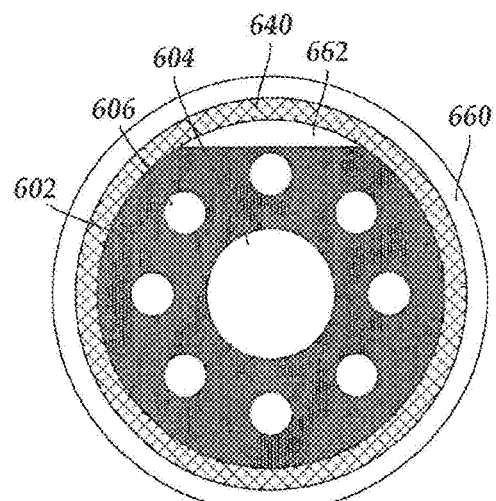
FIG. 6A is a schematic transverse cross-sectional view of one embodiment of a pre-lead, the pre-lead including a multi-lumen conductor guide that defines a central lumen and a plurality of conductor lumens arranged around the central lumen, conductive contacts disposed on the conductor guide and a temporary tube disposed around the conductive contacts and a portion of the conductor guide, according to the invention.
Figure 6B:
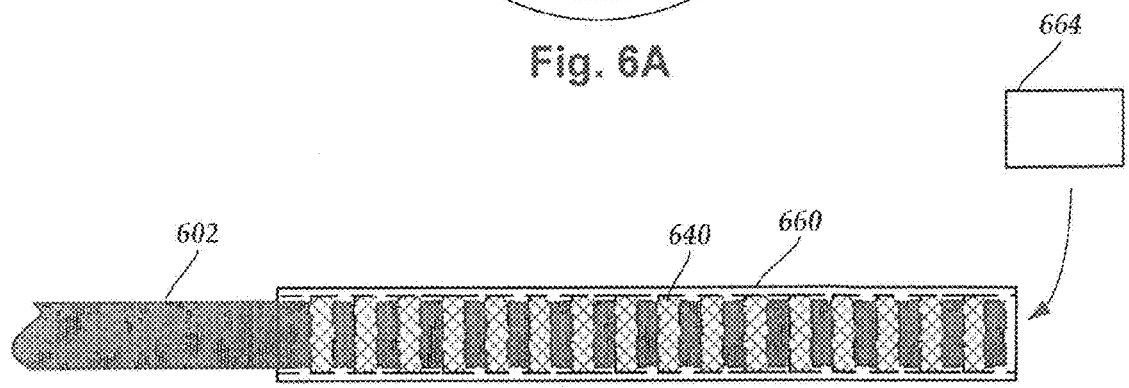
FIG. 6B is a schematic side view of one embodiment of a portion of the pre-lead of FIG. 6A and indicating the introduction of a flowable non-conductive material into the temporary tube, according to the invention.
Figure 6C:
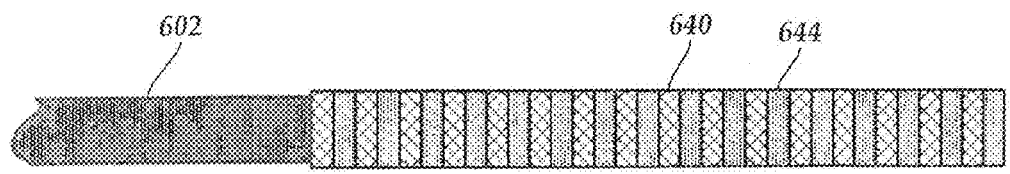
FIG. 6C is a schematic side view of one embodiment of a portion of a lead formed using the components and temporary tube of FIG. 6A, according to the invention.

FIGS. 6A-6C illustrate yet another method of forming a contact array of a lead. A pre-lead includes a multi-lumen conductor guide 602 that defines a central lumen 604 and multiple conductor lumens 606 arranged around the central lumen 604, as illustrated in FIG. 6A. The conductor lumens 606 can have any suitable cross-sectional shape, such as elliptical, oval, rectangular, or the like. In an embodiment, the conductor lumens 606 may be positioned in a radial symmetry around the central lumen 604, where the radial distance of each conductor lumen 606 from the central lumen 604 is a constant.

The conductive contacts 640 are disposed on the multi-lumen conductor guide 602 of the pre-lead, as illustrated in FIGS. 6A and 6B. A number of conductive wires (not shown) are disposed within the multi-lumen conductor guide 602, and are coupled to the conductive contacts 640. Each of the conductive contacts 640 is coupled to one or more conductive wires.

The conductive contacts 640 in the illustrated embodiment are ring-shaped hollow structures. It will be recognized that conductive contacts with other shapes may also be used. In the illustrated embodiment, the conductive contacts 640 have a circular cross-section and the multi-lumen conductor guide 602 has a non-circular cross-section to provide a passage space 662 between the multi-lumen conductor guide 602 and an inner surface of the conductive contacts 640, as illustrated in FIG. 6A. The passage space 662 is configured to allow passage of flowable non-conductive material beneath the conductive contacts.

A temporary tube 660 is slid over the portion of the pre-lead to encompass the conductive contacts 640 and a portion of the multi-lumen conductor guide 602, as illustrated in FIGS. 6A and 6B. The temporary tube 660 is used to retain the flowable non-conductive material 664 introduced into the space between adjacent conductive contacts of the conductive contacts 640 during formation of spacers between the conductive contacts.

The temporary tube 660 may be made of any suitable material including polymeric materials that can be slid onto the pre-lead and removed after the spacers are formed. For example, suitable materials may have sufficient flexibility to slide the temporary tube 660 over the outer surface of the pre-lead. In some embodiments, the temporary tube 660 may be formed of a heat-shrinkable material so that the temporary tube 660 can be slid onto the pre-lead and then heat applied to shrink the temporary tube 660 to seal it against the electrodes 640. In other embodiments, the temporary tube 660 is made of a sufficiently rigid or stiff material to maintain its shape during the introduction of the flowable non-conductive material.

Preferably, the temporary tube 660 supports the flowable non-conductive material 664 introduced into the passage space 662 to flow between the conductive contacts 640 and assists the flowable non-conductive material in acquiring desired shape of spacers upon curing or otherwise solidifying. In addition, the temporary tube 660 is formed of a material that is easily separable from the material of the spacers 644 (FIG. 6C) once they are formed.

When injected or otherwise introduced into the temporary tube 660, the flowable non-conductive material 664 fills the voids between the adjacent pairs of conductive contacts 640 and over the multilumen conductor guide 602. The non-conductive material 664 may also flow into the conductor lumens 606 of the multi-lumen conductor guide 602, filling portions of those conductor lumens, through which no conductive wires pass (this includes that ends of the conductor lumens between the end of the lead the electrode to which the conductor wire within the conductor lumen is attached). The flowable non-conductive material 664 is cured, polymerized, or otherwise solidified using any suitable technique, including, but not limited to, drying, heating, using ultraviolet or visible light, or the like. The specific type of curing method may depend on the type of flowable non-conductive material used. Examples of suitable non-conductive materials 664 may include, but are not limited to, silicone, polyurethane, PEEK, epoxy, and the like or combinations thereof. In one embodiment, the non-conductive material 664 is silicone. In any o f the embodiments described herein, the spacers generated by the methods can have a higher durometer than the material used for the lead body even if the materials of both the spacers and the lead body are the same type (for example, silicone).

After formation of the spacers 644, the temporary tube 660 is removed to expose the conductive contacts 640 and spacers 644, as illustrated in FIG. 6C. Removal of the temporary tube 660 may be achieved by any suitable method including, but not limited to, cutting a slit along the length of the tube and then removing the tube.

Once the temporary tube 660 is removed, any extra non-conductive material 664 deposited over the conductive contacts 640 can be removed, if needed, by any suitable method, such as, for example, grinding (e.g., centerless grinding) or the like. Further, in case where outer diameters of the conductive contacts 640 and the spacers 644 are non-uniform, the conductive contacts 640 and the spacers 644 may be made uniform or otherwise finished by any suitable method including, but not limited to centerless grinding to make the lead, or at least the conductive contact array and spacers, isodiametric.

Figure 7A:
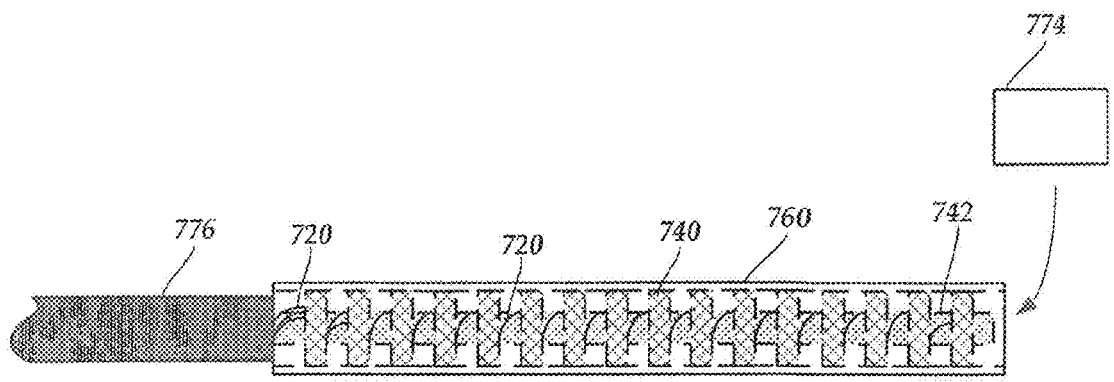
FIG. 7A is a schematic side view of another embodiment of a pre-lead and indicating the introduction of a flowable non-conductive material into a temporary tube disposed around an end of the pre-lead (FIG. 7A only illustrates three conductors for clarity of illustration, but it will be understood that the arrangement can have any number of conductors), according to the invention.
Figure 7B:
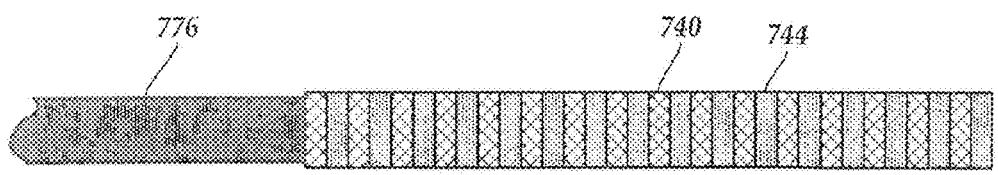
FIG. 7B is a schematic side view of one embodiment of a portion of a lead formed using the components and temporary tube of FIG. 7A, according to the invention.

FIGS. 7A-7B illustrate a further method of forming a contact array of a lead. A pre-lead has a body 776 that includes conductors 720 extending from the body 776. In some embodiments, the body 776 includes a multi-lumen conductor guide that defines a central lumen and multiple conductor lumens arranged around the central lumen such as those described above. A stylet tube 742 can extend from the multi-lumen conductor guide or can be attached thereto. In other embodiments, the body 776 may include a stylet tube 742 that extends through (and out the end of) the body 776 with conductors coiled, or otherwise arranged around, the stylet tube.

As illustrated in FIG. 7A, the stylet tube 742 extends away from the body 776 and the conductors 720 are wrapped or coiled around the stylet tube. (FIG. 7A only illustrates three conductors for clarity of illustration, but it will be understood that the arrangement can have any number of conductors as described above with respect to other embodiments.)

The conductive contacts 740 are disposed over the stylet tube 742 and conductors 720, as illustrated in FIG. 7A. The conductive wires 720 are coupled to the conductive contacts 740. Each of the conductive contacts 740 is coupled to one or more of the conductive wires 720.

The conductive contacts 740 in the illustrated embodiment are ring-shaped hollow structures. It will be recognized that conductive contacts with other shapes may also be used. In the illustrated embodiment, the conductive contacts 740 have a circular cross-section and there is a passage space between the inner surface of the conductive contacts 740 and the conductor wires 720 and stylet tube 742. The passage space is configured to allow passage of flowable non-conductive material beneath the conductive contacts.

A temporary tube 760 is slid over the portion of the pre-lead to encompass the conductive contacts 740, as illustrated in FIG. 7A. The temporary tube 760 is used to retain the flowable non-conductive material 764 introduced into the space between adjacent conductive contacts of the conductive contacts 740 during formation of spacers between the conductive contacts. This temporary tube 760 can be made of the same materials as described above for temporary tube 660.

Preferably, the temporary tube 760 supports the flowable non-conductive material 764 introduced into the passage space to flow between the conductive contacts 740 and assists the flowable non-conductive material in acquiring desired shape of spacers upon curing or otherwise solidifying. In addition, the temporary tube 760 is formed of a material that is easily separable from the material of the spacers 744 (FIG. 7B) once they are formed.

When injected or otherwise introduced into the temporary tube 760, the flowable non-conductive material 764 fills the voids between the adjacent pairs of conductive contacts 740 and over the conductor wires 720 and stylet tube 742. The flowable non-conductive material 764 is cured, polymerized, or otherwise solidified using any suitable technique, including, but not limited to, drying, heating, using ultraviolet or visible light, or the like. The specific type of curing method may depend on the type of flowable non-conductive material used. Examples of suitable non-conductive materials 764 may include, but are not limited to, silicone, polyurethane, PEEK, epoxy, and the like or combinations thereof. In one embodiment, the non-conductive material 664 is silicone. In any of the embodiments described herein, the spacers generated by the methods can have a higher durometer than the material used for the lead body even if the materials of both the spacers and the lead body are the same type (for example, silicone).

After formation of the spacers 744, the temporary tube 760 is removed to expose the conductive contacts 740 and spacers 744, as illustrated in FIG. 7B. Removal of the temporary tube 760 may be achieved by any suitable method including, but not limited to, cutting a slit along the length of the tube and then removing the tube.

Once the temporary tube 760 is removed, any extra non-conductive material 764 deposited over the conductive contacts 740 can be removed, if needed, by any suitable method, such as, for example, grinding (e.g., centerless grinding) or the like. Further, in case where outer diameters of the conductive contacts 740 and the spacers 744 are non-uniform, the conductive contacts 740 and the spacers 744 may be made uniform or otherwise finished by any suitable method including, but not limited to centerless grinding to make the lead, or at least the conductive contact array and spacers, isodiametric.

Figure 8:
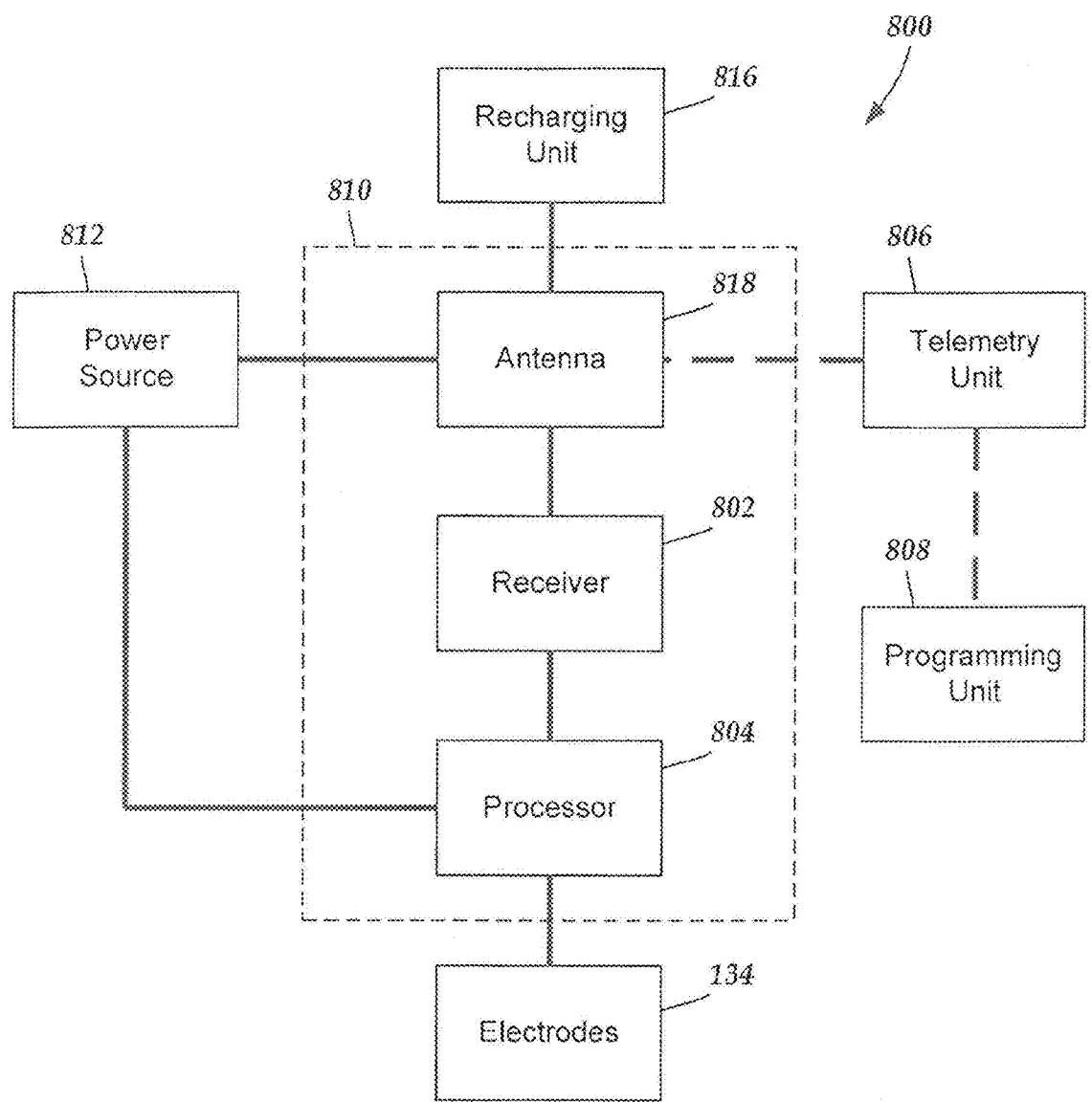
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

In an alternate embodiment, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system 800. A processor 804 is generally included to control the timing and electrical characteristics of the electrical stimulation system 800. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system 800. For example, the signals may be used to modify the pulses of the electrical stimulation system 800 such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system 800 does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making an electrical stimulation lead, the method comprising:
   disposing a plurality of conductive contacts on a conductor guide or stylet tube in a spaced-apart longitudinal arrangement;
   coupling a plurality of conductive wires disposed within the conductor guide or around the stylet tube to the plurality of conductive contacts, wherein each conductive contact is coupled to at least one of the conductive wires;
   sliding a temporary tube over the plurality of conductive contacts, wherein the temporary tube is made of polymeric material and has a length;
   introducing a flowable non-conductive material into the temporary tube and flowing the flowable non-conductive material between adjacent pairs of conductive contacts and over the conductor guide or stylet tube;
   forming at least one spacer from the flowable non-conductive material to separate the conductive contacts; and
   cutting a slit along the length of the temporary tube and removing the temporary tube to expose the conductive contacts.

2. The method of claim 1, wherein disposing the plurality of conductive contacts comprises disposing a plurality of electrodes on the conductor guide in the spaced-apart longitudinal arrangement.

3. The method of claim 1, wherein disposing the plurality of conductive contacts comprises disposing a plurality of terminals on the conductor guide in the spaced-apart longitudinal arrangement.

4. The method of claim 1 wherein forming at least one spacer comprises solidifying the flowable non-conductive material.

5. The method of claim 1, wherein forming at least one spacer comprises curing the flowable non-conductive material.

6. The method of claim 1, wherein the conductive contacts have a circular ring-shaped cross-section and the conductor guide has a non-circular cross-section that provides at least one passage space between the conductor guide and an inner surface of the conductive contacts.

7. The method of claim 2, further comprising grinding the electrodes and the at least one spacer to provide an isodiametric lead.

8. The method of claim 1, wherein the flowable non-conductive material comprises silicone.

9. The method of claim 1, wherein the conductor guide comprises a plurality of conductor lumens and wherein introducing the flowable non-conductive material comprises flowing the non-conductive material into the conductor lumens to fill portions of the conductor lumens that do not contain one of the conductive wires.

10. The method of claim 1, wherein introducing the flowable non-conductive material comprises injecting the flowable non-conductive material into the temporary tube using a syringe.

* * * * *